(12) United States Patent
Bibber

(10) Patent No.: US 8,388,825 B2
(45) Date of Patent: *Mar. 5, 2013

(54) CONVERSION COATING FOR ALUMINUM AND ITS ALLOYS AND ARTICLES THEREOF

(75) Inventor: John W. Bibber, Batavia, IL (US)

(73) Assignee: Sanchem, Inc., Chicago, IL (US)

( * ) Notice: Subject to any disclaimer, the term of this patent is extended or adjusted under 35 U.S.C. 154(b) by 6 days.

This patent is subject to a terminal disclaimer.

(21) Appl. No.: 13/017,341

(22) Filed: Jan. 31, 2011

(65) Prior Publication Data

US 2011/0120876 A1    May 26, 2011

Related U.S. Application Data

(62) Division of application No. 11/972,020, filed on Jan. 10, 2008, now abandoned.

(51) Int. Cl.
*C23C 28/00* (2006.01)
(52) U.S. Cl. ...................................... 205/198
(58) Field of Classification Search .................. 428/457; 106/14.25, 14.22, 25; 205/198, 204
See application file for complete search history.

(56) References Cited

U.S. PATENT DOCUMENTS

| 4,840,820 A * | 6/1989 | Schultz et al. ............. 427/305 |
| 5,693,153 A * | 12/1997 | Rosengard ............. 148/272 |
| 6,830,821 B2 * | 12/2004 | Bibber .................. 428/457 |
| 2006/0124466 A1 | 6/2006 | Xu et al. |

OTHER PUBLICATIONS

Unknown Author, Dairy Chemistry and Physics, Published Jan. 1, 2006.

* cited by examiner

*Primary Examiner* — Jennifer Michener
*Assistant Examiner* — Eli Mekhlin
(74) *Attorney, Agent, or Firm* — James B. Conte; Husch Blackwell LLP

(57) ABSTRACT

I provide a non-toxic protein and protein compound conversion coated metal article, a painted or plated non-toxic protein and protein compound conversion coated metal article, the aqueous coating solution to provide the in-situ conversion protective coating, and a process of preparing the article. The article is a metal selected from the group consisting of aluminum and aluminum alloy. The solution has a pH of 3.0 to 12.0 and preferably 4.0 to 10.0 and a protein and protein compound concentration of 0.1 to 10% by weight and the protein and protein compound have a molecular mass of 16,700 to 1,000,000.

11 Claims, No Drawings

CONVERSION COATING FOR ALUMINUM AND ITS ALLOYS AND ARTICLES THEREOF

CROSS-REFERENCE TO RELATED APPLICATION

This is a division of application Ser. No. 11/972,020, filed Jan. 10, 2008 now abandoned, whose disclosures are incorporated herein by reference.

FIELD OF INVENTION

The present invention relates to the application and generation of a non-toxic and environmentally safe protein or protein compounds based conversion coating for aluminum and its alloys. More particularly the invention relates to a composition and a method of conversion coating aluminum and its alloys with a non-toxic and environmentally friendly protein composition that reacts in-situ with the surface of the metal to generate a conversion coating that incorporates the metal.

BACKGROUND OF THE INVENTION

The chemical conversion coating of aluminum and its alloys is known in the art as a process whereby the surface of the metal is chemically converted to a surface that more easily accepts applied coatings, i.e. paint, and for increases the corrosion resistance of the metal. An industry accepted process for the conversion coating of aluminum and its alloys makes use of known carcinogens such as chromates (see: MIL-DTL-80716B and/or ASTM B449). As a result, chromates and related toxic materials are being displaced by less toxic alternatives. Alternative conversion coatings in current use are based upon phosphates and/or anodizing or oxidation of the metal. Oxidized or phosphate generated conversion coatings tend to be brittle. In addition the processes require the use of long involved cleaning procedures involving toxic fluorides (see: Biestek, T., and Weber, J.: "Electrolytic and Chemical Conversion Coatings", Portculis Press. Ltd., Queensway House, 2 Queensway, Redhill Surrey, RH1 1QS, 1976 and Wernick, S., Pinner. R. "The Surface Treatment and Finishing of Aluminum and its Alloys", ASM International Metals Park, Ohio, 1987).

A typical A typical process for Aluminum and its alloys would involve: Hot alkaline soak cleaner at about 150 degrees F. for three to five minutes, D.I water rinse, dip in a strong acid solution to remove unwanted alloyed metals and/or metal oxides, rinse in D.I. water, conversion coating in a hexavalent chromium based solution and a final water rinse. Such a surface need to painted shortly after being produced as it will quickly form a hydrophobic surface and as a result will not easily accept applied coatings. Electroplating or non-electrolytic plating of aluminum and its alloys requires all of the above steps (with the exception of processing in a chromate conversion coating solution) and the application of an immersion zinc coating to provide for a uniform and even plating surface. These processes are rather difficult to properly apply and even with the use of the above processing steps, the plating of aluminum and its alloys is a very difficult process. (see: http://www.pfonline.com/articles/019601.html).

SUMMARY OF THE INVENTION

This invention is directed towards making use of the corrosion resistant and adhesion characteristics of protein compounds or protein to generated conversion coatings on aluminum and its alloys. The preferred coating is water based. The water based coating generates no volatile organic carbon compounds. In addition the coating does not contain any known toxic substances and will not generate any known toxic substances. The coating is very thin (less then 600 nm.) and as a result is sufficiently electrically conductive for use in aerospace applications.

This invention provides an aqueous conversion coating composition for the aluminum and its alloys metals, to generate an outer protective in-situ coating on the aluminum and aluminum alloy. The protective conversion coating composition has as its essential ingredients thereof protein compounds or proteins that will react with the aluminum and aluminum alloy to generate in-situ a coating that will more easily accept applied coatings and provide for a more corrosion resistant surface.

The invention also provides non-toxic aluminum and aluminum alloy aqueous coating composition where in the essential ingredient is non-toxic protein to provide an outer protective coating for the non-toxic aluminum and aluminum alloy and wherein the protein has a molecular mass of from 16,700 to 1,000,000 and provides a concentration of 0.1 to 10%, the pH of the composition is from 4.0 to 10.0, the protein is selected from the group consisting of casein, dried egg white, gelatin, serum albumin, hemoglobin, lacto globulin, gliadin. and mixtures thereof, and the composition provides an in-situ conversion coating on the metal that will provide oxidation resistance to the metal for at least 5 days at room temperature and allow the conversion coated metal to be painted such that a cured painted metal showed no signs of blistering and no signs of adhesion failure, and the composition provides an in-situ conversion coating on the metal that allows the conversion coated metal to be electroless plated and then placed in an oven at 350° F. for one half hour, removed and immediately quenched in water and the plated metal showed no signs of blistering or loss of adhesion.

The invention further provides a metal article wherein the metal is selected from the group consisting of aluminum and aluminum alloy and the metal having thereon an in-situ non-toxic protein conversion coating wherein the protein has a molecular mass of 16,700 to 1,000,000 and is selected from the group consisting of casein, dried egg white, gelatin, serum albumin, hemoglobin, lacto globulin, gliadin. and mixtures thereof, and the conversion coated metal has oxidation resistance for at least 5 days at room temperature and when the conversion coated metal is painted or electroless metal plated, the cured painted conversion coated metal showed no signs of blistering and no signs of adhesion failure, and the electroless plated conversion coated metal when placed in an oven at 350° F. for one half hour, removed and immediately quenched in water showed no signs of blistering and no signs of adhesion failure.

Still another feature of the present invention is to provide a process of preparing the metal article wherein the metal selected from the group consisting of aluminum and aluminum alloy, cleaning the metal article, making the metal a cathode or anode of an electrolytic cell containing an aqueous protein solution wherein the protein has a molecular mass of from 16,700 to 1,000,000 and is selected from the group consisting of casein, dried egg white, gelatin, serum albumin, hemoglobin, lacto globulin, gliadin. and mixtures thereof, and the aqueous solution has a protein concentration of 0.1 to 10% by weight, and a pH of the composition is from 4.0 to 10.0; forming an in-situ protein conversion coating on the metal, curing the conversion coated metal and painting or electroless plating the conversion coated metal wherein the cured painted conversion coated metal showed no signs of blistering and no signs of adhesion failure, and the electroless plated conversion coated metal when placed in an oven at 350° F. for one half hour, removed and immediately quenched in water showed no signs of blistering and no signs of adhesion failure.

DETAILED DESCRIPTION OF THE INVENTION

An aluminum and aluminum alloy is afforded corrosion resistant and receptive to the application of secondary coatings, i.e. paint, by having thereon an outer protective coating of proteins or protein compounds reacted with the aluminum and aluminum alloy.

The protein generated conversion coatings are formed by making the aluminum or aluminum alloy as the cathode or anode of an electrolytic cell in an electrolyte solution of the proteins or protein compounds made soluble by dissolving the materials in an acid or a basic solution.

Additional wetting agents or complexing agents may be added as needed to enhance their adhesive and/or protective ability. The amine and/or acid functionality of the protein and/or protein compounds will then attach themselves to the aluminum or aluminum alloy and further react with the aluminum or aluminum alloy so as to form in a metal compound on the surface of the aluminum or aluminum alloy that is strongly bonded to the aluminum of aluminum alloy, and provides for a corrosion resistant surface that is receptive to the application of secondary coatings, i.e. paint.

To aid in the application of the protein and/or protein compounds the

PH of the solution may be varied depending upon the particular metal being treated. Also, the concentration of the proteins and/or protein compounds may be varied depending upon the thickness of the coating so desired and the conductivity of the solution varied to increase or decrease the rate of deposition of the proteins and/or protein compounds. The lower limit of the concentration of these solutions is purely an economic matter. The lower the concentration of the ingredients to be deposited, the longer it will take to produce a film of sufficient thickness (about 600 nm.) to provide a good adhesive base and sufficient resistance to oxidation. The upper limits on the concentration of the solution will be the saturation point of the mixture in question.

In theory any PH may be used, but aluminum is quite soluble in strongly acid solutions and/or strongly basic solutions. The most suitable pH range is 3.0 to 12.0 with the preferred pH 4.0 to 10.0. Temperature is of no concern to the process. The voltage must be above the reduction potential of the protein complexes and sufficient to maintain the required current density. Various other non-interfering materials may be added to the protein solutions to prevent biological attack, increase conductivity or control the pH (buffers) as long as these materials do not act to prevent proper film formation.

The basic composition used to form the corrosion resistant and more adhesive surface is a water based solution of 0.1% to 10% protein and/or protein compounds. The proteins and/or protein compounds preferably have a molecular mass of from 16,700 to 1,000,000. A widely used source of these proteins are milk and egg whites with casein from milk being the most preferred source as this is an excellent film forming source of proteins. Casein is quite environmentally friendly, non-toxic, inexpensive and readily available. Other useful protein sources are serum albumin, hemoglobin, lacto globulin and gliadin.

The aqueous solution generally contains from one to five percent proteins and/or protein compounds. The advantages gained by using my protein based conversion coatings are a total lack of any toxic and/or environmentally unfriendly compounds, excellent paint and/or plating adhesion on the aluminum and aluminum alloy, a simpler methods of application.

The industry standard for conversion coatings on aluminum and aluminum alloy, in terms of paint adhesion and corrosion resistance, continues to be the chromate generated coatings. As such the adhesion and corrosion resistance of these coatings is directly compared to chromate based systems whenever possible. The aluminum used in these examples is pure aluminum and the aluminum alloy "7075-T6", as it represents an extreme example of paint and/or plating adhesion properties. In addition it is used in many aerospace applications

EXAMPLE 1

A 0.032 inch thick 3.0 inch by 10 inch panel of "7075-T6" aluminum Alloy was cleaned in a mild alkaline cleaner at 150° F. for three minutes, rinsed in D.I. water, soaked in a 20% nitric acid solution at 100° F. for two minutes to remove any alloyed metals or metal oxides, rinsed again in D.I. water and then made the cathode of an electrolytic cell consisting of:

1.0% Casein
0.038% potassium hydroxide
0.3% potassium salt of Glycolic acid
Phosphoric acid used to adjust PH to 7.5
Balance water The proteins compounds and/or proteins were plated out on the surface of the metal with a current density of 14 amps per square foot for four seconds. The metal was then rinsed, dried and allowed to sit in the open for one week before being painted with an Epoxy Polyamide primer as outlined in MIL-DTL-5541F. When cured, the panel was tested for adhesion as outlined in the specification and showed no signs of adhesion failure or blistering.

EXAMPLE 2

A 0.032 inch thick 3.0 inch by 10 inch panel of "7075-T6" aluminum alloy was cleaned in a mild alkaline cleaner at 150° F. for three minutes, rinsed in D.I. water, soaked in a 20% nitric acid solution at 100° F. for two minutes to remove any alloyed metals or metal oxides, rinsed again in D.I. water and then made the cathode of an electrolytic cell consisting of:

1.0% Casein
0.25% Phosphoric acid (85%) to adjust the PH to 3.0
Balance D.I. water The proteins compounds and/or proteins were plated out on the surface of the metal with a current density of 14 amps per square foot for four seconds. The metal was then rinsed, dried and allowed to sit in the open for one week before being painted with an Epoxy Polyamide primer as outlined in MIL-DTL-5541F. When cured the panel was tested for adhesion as outlined in the specification and showed no signs of adhesion failure or blistering.

EXAMPLE 3

A 0.032 inch thick, 3.0 inch by 10 inch panel of "1175" aluminum alloy (pure aluminum) was cleaned in a mild alkaline cleaner at 150° F. for three minutes, rinsed in D.I. water and then made the cathode of an electrolytic cell consisting of:

1.0% Casein
0.50% potassium hydroxide to adjust the PH to 9.0

Balance D.I. water

The proteins compounds and/or proteins were plated out on the surface of the metal with a current density of 14 amps per square foot for four seconds. The metal was then rinsed, dried and allowed to sit in the open for one week before being painted with a commercial solvent based polyurethane paint. After being allowed to cure the coating was tested for paint adhesion according to ASTM-D3359 and tested for wet paint adhesion according to AAMA 2605. There were no signs of paint adhesion failure.

EXAMPLE 4

A 0.032 inch thick, 3.0 inch by 10 inch panel of "1175" aluminum alloy (pure aluminum) was cleaned in a mild alkaline cleaner at 150° F. for three minutes, rinsed in D.I. water and then made the cathode of an electrolytic cell consisting of:
  2.0% dried egg white
  Enough 2-amino-methyl-1-propanol to bring the PH to 11.0
  Balance D.I. water The proteins and/or proteins compounds were plated out on the surface of the metal with a current density of 14 amps per square foot for two seconds. The metal was then rinsed, dried and then powder coated with a polyester coating and cured at 400° F. for 15 minutes. Paint adhesion tests according to AAMA 2605 showed no loss of paint adhesion.

EXAMPLE 5

A 0.032 inch thick, 3.0 inch by 10 inch panel of "1175" aluminum alloy (pure aluminum) was cleaned in a mild alkaline cleaner at 150° F. for three minutes, rinsed in D.I. water and then made the cathode of an electrolytic cell consisting of:
  2.0% gelatin
  Enough potassium Hydroxide to bring the PH to 12.0
  Balance D.I. water The proteins and/or proteins compounds were plated out on the surface of the metal with a current density of 14 amps per square foot for two seconds. The metal was then rinsed with D.I. water, dried and then powder coated with a polyamide coating and cured at 400° F. for 15 minutes. Paint adhesion tests according to AAMA 2605 showed no loss of paint adhesion.

EXAMPLE 6

Example 5
A 0.032 inch thick, 3.0 inch by 10 inch panel of "7075-T6" aluminum alloy was cleaned in a mild alkaline cleaner at 150° F. for three minutes, rinsed in D.I. water, soaked in a 20% nitric acid solution at 100 degrees F. for two minutes to remove unwanted alloy metals or metal oxides, rinsed in D.I. water and then made the cathode of an electrolytic cell consisting of:
  4.0% Casein
  1.5% potassium hydroxide
  1.2% potassium salt of Glycolic acid
  Enough Phosphoric acid to bring the PH to 6.0
  Balance D.I. water The proteins and/or proteins compounds were plated out on the surface of the metal with a current density of 14 amps per square foot for two seconds. The metal was then rinsed, in D.I. water and placed in a PH 5.0 fluoride based electroless nickel plating bath for one hour to plate out a 0.001 inch thick film of electroless nickel. The plated panel was then placed in an oven at 350° F. for one half hour, removed and immediately quenched in water as outlined in MIL-C-16074E. There was no blistering or loss of nickel adhesion to the metal panel

EXAMPLE 7

A 0.032 inch thick, 3.0 inch by 10 inch panel of "1175" aluminum alloy (pure aluminum) was cleaned in a mild alkaline cleaner at 150° F. for three minutes, rinsed in D.I. water and then made the cathode of an electrolytic cell consisting of:
  4.0% Casein
  1.5% potassium hydroxide
  Enough Phosphoric acid to bring the PH to 7.0
  Balance D.I. water The proteins and/or proteins compounds were plated out on the surface of the metal with a current density of 14 amps per square foot for two seconds. The metal was then rinsed, in D.I. water and placed in a PH 5.0 fluoride based electroless nickel plating bath for one hour to plate out a 0.001 inch thick film of electroless nickel. The plated panel was then placed in an oven at 350° F. for one half hour, removed and immediately quenched in water as outlined in MIL-C-16074E. There was no blistering or loss of nickel adhesion to the metal panel.

EXAMPLE 8

A 0.032 inch thick, 3.0 inch by 10 inch panel of "7075-T6" aluminum alloy was cleaned in a mild alkaline cleaner at 150 degrees F. for three minutes, rinsed in D.I. water, soaked in a 20% nitric acid solution at 100° F. for two minutes to remove unwanted alloy metals or metal oxides, rinsed in D.I. water and then made the anode of an electrolytic cell consisting of:
  4.0% Casein
  1.5% potassium hydroxide
  1.2% potassium salt of Glycolic acid
  Enough Phosphoric acid to bring the PH to 6.0
  Balance D.I. water The proteins and/or proteins compounds were plated out on the surface of the metal with a current density of 14 amps per square foot for two seconds. The metal was then rinsed, in D.I. water and placed in a PH 5.0 fluoride based electroless nickel plating bath for one hour to plate out a 0.001 inch thick film of electroless nickel. The plated panel was then placed in an oven at 350° F. for one half hour, removed and immediately quenched in water as outlined in MIL-C-16074E. There was no blistering or loss of nickel adhesion to the metal panel

EXAMPLE 9

A 0.032 inch thick, 3.0 inch by 10 inch panel of "1175" aluminum alloy (pure aluminum) was cleaned in a mild alkaline cleaner at 150° F. for three minutes, rinsed in D.I. water and then made the anode of an electrolytic cell consisting of:
  4.0% Casein
  1.5% potassium hydroxide
  Enough Phosphoric acid to bring the PH to 7.0
  Balance D.I. water The proteins and/or proteins compounds were plated out on the surface of the metal with a current density of 14 amps per square foot for two seconds. The metal was then rinsed, in D.I. water and placed in a PH 5.0 fluoride based electroless nickel plating bath for one hour to plate out a 0.001 inch thick film of electroless nickel. The plated panel was then placed in an oven at 350 degrees F. for one half hour, removed and immediately quenched in water as outlined in MIL-C-16074E. There was no blistering or loss of nickel adhesion to the metal panel.

While the invention has been described with a high degree of particularity, it will be appreciated by those skilled in the art that modifications may be made thereto. Therefore, it is to be understood that the present invention is not limited to the embodiments described above, but encompasses any and all embodiments within the scope of the following claims.

I claim:

1. A process for plating an aluminum article or an aluminum alloy article comprising:
   a) preparing the surface of the aluminum or aluminum alloy article by treating the aluminum or aluminum alloy article to remove unwanted alloyed metals or metal oxides;
   b) making the aluminum article or the aluminum alloy article a cathode or an anode of an electrolytic cell containing an aqueous solution or dispersion of a protein;
   c) applying an electric current to the electrolytic cell wherein the protein becomes chemically bonded directly to the aluminum article or the aluminum alloy article;
   d) placing the protein-bonded aluminum article or the protein-bonded aluminum alloy article into an electroless metal plating bath containing a metal; and
   e) electroless plating the metal onto the protein-bonded aluminum article or the protein-bonded aluminum alloy article to produce a metal-plated aluminum article or a metal-plated aluminum alloy article.

2. The process of claim 1 wherein the protein has a molecular mass in the range of 16,700 to 1,000,000 and is present in the aqueous solution at a concentration of 0.1 to 10%.

3. The process of claim 1 wherein the protein is selected from the group consisting of casein, dried egg white, gelatin, serum albumin, hemoglobin, lacto globulin, gliadin and mixtures thereof.

4. The process of claim 1 wherein the metal-plated aluminum article or the metal-plated aluminum alloy article when placed in an oven at 350° F. for one half hour, removed and immediately quenched in water exhibits no signs of blistering and no signs of adhesion failure.

5. The process of claim 1 wherein the aqueous solution has a pH in the range of about 3.0 to about 12.0.

6. The process of claim 1 wherein the aqueous solution has a pH in the range of about 4.0 to about 10.0.

7. The process of claim 1 wherein the aqueous solution further comprises a buffering agent, an agent to prevent biological attacks of the protein, or an agent to increase the conductivity of the aqueous solution.

8. The process of claim 1 wherein the protein comprises casein.

9. The process of claim 1 wherein the protein comprises a mixture of casein and albumin.

10. The process of claim 1 wherein the protein comprises a mixture of casein and gelatin.

11. The process of claim 1 wherein the metal within the electroless plating bath is nickel.

* * * * *